(12) United States Patent
Ramadan et al.

(10) Patent No.: US 9,192,561 B2
(45) Date of Patent: Nov. 24, 2015

(54) COMPOSITIONS CONTAINING HYPERBRANCHED POLYOL AND ACRYLIC FILM FORMER

(75) Inventors: Fatima Ramadan, Marlboro, NJ (US); Yoriko Kawaratani, Chuou-ku (JP); Hy Si Bui, Piscataway, NJ (US); Kimberly Bradshaw, Monmouth Junction, NJ (US)

(73) Assignee: L'Oreal, Paris (FR)

( * ) Notice: Subject to any disclaimer, the term of this patent is extended or adjusted under 35 U.S.C. 154(b) by 411 days.

(21) Appl. No.: 13/107,337

(22) Filed: May 13, 2011

(65) Prior Publication Data

US 2011/0280817 A1 Nov. 17, 2011

Related U.S. Application Data

(60) Provisional application No. 61/334,880, filed on May 14, 2010, provisional application No. 61/334,904, filed on May 14, 2010.

(51) Int. Cl.
| | |
|---|---|
| *A61K 8/92* | (2006.01) |
| *A61Q 1/06* | (2006.01) |
| *A61K 8/81* | (2006.01) |
| *A61K 8/31* | (2006.01) |
| *A61K 8/37* | (2006.01) |

(52) U.S. Cl.
CPC ............... *A61K 8/8111* (2013.01); *A61K 8/31* (2013.01); *A61K 8/37* (2013.01); *A61K 8/8152* (2013.01); *A61Q 1/06* (2013.01); *A61K 2800/594* (2013.01)

(58) Field of Classification Search
CPC ......... A61K 8/31; A61K 8/37; A61K 8/8152; A61K 8/8111; A61K 2800/594; A61Q 1/06
See application file for complete search history.

(56) References Cited

U.S. PATENT DOCUMENTS

| | | | | |
|---|---|---|---|---|
| 7,314,904 B2 * | 1/2008 | Nadolsky et al. | ........... | 526/307.5 |
| 7,423,104 B2 * | 9/2008 | Lion | ........... | 526/317.1 |
| 7,875,265 B2 | 1/2011 | Blin et al. | | |
| 8,119,110 B2 | 2/2012 | Blin et al. | | |
| 2006/0093568 A1 | 5/2006 | Blin et al. | | |
| 2006/0115444 A1 | 6/2006 | Blin et al. | | |
| 2006/0147402 A1 | 7/2006 | Blin et al. | | |
| 2006/0165626 A1 * | 7/2006 | Ricard et al. | ........... | 424/70.11 |
| 2007/0110702 A1 * | 5/2007 | Ehara | ........... | 424/70.31 |
| 2007/0134181 A1 | 6/2007 | Shimizu et al. | | |
| 2007/0258932 A1 * | 11/2007 | Bui et al. | ........... | 424/70.11 |
| 2008/0025934 A1 | 1/2008 | Lebre et al. | | |
| 2009/0130037 A1 | 5/2009 | Thevenet et al. | | |
| 2010/0310489 A1 | 12/2010 | Barba | | |
| 2010/0330012 A1 | 12/2010 | Bui et al. | | |
| 2010/0330015 A1 | 12/2010 | Bui et al. | | |
| 2010/0330016 A1 | 12/2010 | Bui et al. | | |
| 2010/0330017 A1 | 12/2010 | Bui et al. | | |
| 2010/0330022 A1 | 12/2010 | Bui et al. | | |
| 2010/0330024 A1 | 12/2010 | Bui et al. | | |
| 2011/0020254 A1 | 1/2011 | Bui et al. | | |
| 2011/0020255 A1 | 1/2011 | Bui et al. | | |
| 2011/0020256 A1 | 1/2011 | Bui et al. | | |
| 2011/0020257 A1 | 1/2011 | Bui et al. | | |
| 2011/0020260 A1 | 1/2011 | Bui et al. | | |
| 2011/0020261 A1 | 1/2011 | Bui et al. | | |
| 2011/0020263 A1 | 1/2011 | Ilekti et al. | | |
| 2011/0021681 A1 | 1/2011 | Bui et al. | | |
| 2011/0021683 A1 | 1/2011 | Bui et al. | | |
| 2011/0038819 A1 | 2/2011 | Bui et al. | | |
| 2011/0223122 A1 | 9/2011 | Bui et al. | | |
| 2011/0223123 A1 | 9/2011 | Bui et al. | | |
| 2011/0280820 A1 | 11/2011 | Bui et al. | | |
| 2011/0286950 A1 | 11/2011 | Bui et al. | | |
| 2011/0286951 A1 | 11/2011 | Bui et al. | | |
| 2011/0293550 A1 | 12/2011 | Bui et al. | | |
| 2011/0311467 A1 | 12/2011 | Bui et al. | | |
| 2012/0004327 A1 | 1/2012 | Bui et al. | | |
| 2012/0107263 A1 | 5/2012 | Bui et al. | | |
| 2012/0171137 A1 | 7/2012 | Bradsaw et al. | | |
| 2012/0171139 A1 | 7/2012 | Bradshaw et al. | | |

FOREIGN PATENT DOCUMENTS

KR 20100129713 * 5/2007

OTHER PUBLICATIONS

Ilekti, P. et al. Cosmetic composition containing block polymer and non-volatility ester oil, KR 2010 0129713, published: May 2007; Machine English Translation.*
U.S. Appl. No. 13/729,631, filed Dec. 28, 2012, Kawaratani, et al.
U.S. Appl. No. 13/107,373, filed May 13, 2011, Kawaratani, et al.
U.S. Appl. No. 13/107,305, filed May 13, 2011, Ramadan, et al.
U.S. Appl. No. 14/354,719, filed Apr. 28, 2014, Bukawa, et al.
U.S. Appl. No. 14/359,791, filed May 21, 2014, Bui, et al.
U.S. Appl. No. 14/363,215, filed Jun. 5, 2014, Bukawa, et al.

* cited by examiner

*Primary Examiner* — Johann R Richter
*Assistant Examiner* — Genevieve S Alley
(74) *Attorney, Agent, or Firm* — Oblon, McClelland, Maier & Neustadt, L.L.P.

(57) ABSTRACT

The invention relates to a composition, especially a cosmetic composition, comprising at least one hyperbranched polyol and at least one acrylic film forming agent, as well as to methods of using such compositions.

20 Claims, No Drawings

US 9,192,561 B2

COMPOSITIONS CONTAINING HYPERBRANCHED POLYOL AND ACRYLIC FILM FORMER

CROSS-REFERENCE TO RELATED APPLICATIONS

This application claims the benefit of priority under 35 U.S.C. §119(e) from U.S. Provisional Application Ser. Nos. 61/334,880 and 61/334,904, both filed May 14, 2010, the entire contents of which are hereby incorporated by reference.

FIELD OF THE INVENTION

The present invention relates to compositions comprising at least one hyperbranched polyol and at least one acrylic film former. Among other improved or beneficial properties, these compositions have surprisingly good wear, texture, shine (initial and long lasting) and feel properties.

DISCUSSION OF THE BACKGROUND

Many cosmetic compositions, including pigmented cosmetics such as foundations, concealers, lipsticks, and mascaras, and other cosmetic and sunscreen compositions, have been formulated in an attempt to posses long wearing properties upon application. Unfortunately, many of these compositions do not possess long lasting shine properties. Moreover, shiny compositions oftentimes do not possess good wear and/or comfort properties.

Such compositions can contain a large amount of film forming agents to achieve long wear properties, possibly in combination with volatile solvents. However, these formulations generally possess poor shine characteristics, both initially and over time.

Alternatively, two step products have been developed, using a topcoat to provide shine and/or comfort to a basecoat which is matte and/or dry.

Thus, there remains a need for improved cosmetic compositions having improved cosmetic properties, particularly good wear, feel, shine and texture characteristics upon application.

Accordingly, one aspect of the present invention is a care and/or makeup and/or treatment composition for keratinous materials which has good cosmetic properties such as, for example, good shine, feel, wear and/or texture properties upon application.

SUMMARY OF THE INVENTION

The present invention relates to compositions comprising at least one hyperbranched polyol and at least one acrylic film former. Preferably, the compositions are anhydrous. The compositions can further comprise at least one tackifier, if desired.

The present invention also relates to colored compositions comprising at least one coloring agent, at least one hyperbranched polyol and at least one acrylic film former. Such colored compositions can be, for example, cosmetic compositions such as lip compositions (for example, lipstick or liquid lip colors), mascaras, eyeshadows or foundations. Preferably, the compositions are anhydrous. The compositions can further comprise at least one tackifier, if desired.

The present invention also relates to methods of treating, caring for and/or making up keratinous material (for example, skin, eyes, eyelashes or lips) by applying compositions of the present invention to the keratinous material in an amount sufficient to treat, care for and/or make up the keratinous material.

The present invention also relates to methods of enhancing the appearance of keratinous material (for example, skin, eyes, eyelashes, or lips) by applying compositions of the present invention to the keratinous material in an amount sufficient to enhance the appearance of the keratinous material.

The present invention further relates to compositions having improved cosmetic properties such as, for example, increased anti-smudging properties, increased long wear properties, and/or better texture, shine (initial and/or long lasting) and/or feel upon application. Preferably, the compositions are anhydrous. The compositions can further comprise at least one tackifier, if desired.

The present invention also relates to methods of improving the feel, shine (initial and/or long lasting) and/or texture properties of a composition upon application to a keratin material comprising adding to a composition (for example, a lip composition) at least one hyperbranched polyol and at least one acrylic film former.

It is to be understood that both the foregoing general description and the following detailed description are exemplary and explanatory only, and are not restrictive of the invention.

DETAILED DESCRIPTION OF THE INVENTION

As used herein, the expression "at least one" means one or more and thus includes individual components as well as mixtures/combinations.

Other than in the operating examples, or where otherwise indicated, all numbers expressing quantities of ingredients and/or reaction conditions are to be understood as being modified in all instances by the term "about," meaning within 10% to 15% of the indicated number.

"Film former" or "film forming agent" as used herein means a polymer or resin that leaves a film on the substrate to which it is applied, for example, after a solvent accompanying the film former has evaporated, absorbed into and/or dissipated on the substrate.

"Transfer resistance" as used herein refers to the quality exhibited by compositions that are not readily removed by contact with another material, such as, for example, a glass, an item of clothing or the skin, for example, when eating or drinking. Transfer resistance may be evaluated by any method known in the art for evaluating such. For example, transfer resistance of a composition may be evaluated by a "kiss" test. The "kiss" test may involve application of the composition to lips followed by rubbing a material, for example, a sheet of paper, against the lips after expiration of a certain amount of time following application, such as 2 minutes after application. Similarly, transfer resistance of a composition may be evaluated by the amount of product transferred from a wearer to any other substrate, such as transfer from the lips of an individual to a collar when putting on clothing after the expiration of a certain amount of time following application of the composition to the lips. The amount of composition transferred to the substrate (e.g., collar, or paper) may then be evaluated and compared. For example, a composition may be transfer resistant if a majority of the product is left on the wearer's lips. Further, the amount transferred may be compared with that transferred by other compositions, such as commercially available compositions. In a preferred embodiment of the present invention, little or no composition is transferred to the substrate from the lips.

"Long wear" compositions as used herein, refers to compositions where color remains the same or substantially the same as at the time of application, as viewed by the naked eye, after an extended period of time. Long wear properties may be evaluated by any method known in the art for evaluating such properties. For example, long wear may be evaluated by a test involving the application of a composition to lips and evaluating the color of the composition after an extended period of time. For example, the color of a composition may be evaluated immediately following application to lips and these characteristics may then be re-evaluated and compared after a certain amount of time. Further, these characteristics may be evaluated with respect to other compositions, such as commercially available compositions.

"Substituted" as used herein, means comprising at least one substituent. Non-limiting examples of substituents include atoms, such as oxygen atoms and nitrogen atoms, as well as functional groups, such as hydroxyl groups, ether groups, alkoxy groups, acyloxyalky groups, oxyalkylene groups, polyoxyalkylene groups, carboxylic acid groups, amine groups, acylamino groups, amide groups, halogen containing groups, ester groups, thiol groups, sulphonate groups, thiosulphate groups, siloxane groups, and polysiloxane groups. The substituent(s) may be further substituted.

"Volatile", as used herein, means having a flash point of less than about 100° C.

"Non-volatile", as used herein, means having a flash point of greater than about 100° C.

"Anhydrous" means the compositions contain less than 1% water. Preferably, the compositions of the present invention comprising the at least one acrylic thickener contain no water.

The composition of the present invention may be in any form, either liquid or non-liquid (semi-solid, soft solid, solid, etc.). For example, it may be a paste, a solid, a gel, or a cream. It may be an emulsion, such as an oil-in-water or water-in-oil emulsion, a multiple emulsion, such as an oil-in-water-in-oil emulsion or a water-in-oil-in-water emulsion, or a solid, rigid or supple gel. The composition of the invention may, for example, comprise an external or continuous fatty phase. The composition can also be a molded composition or cast as a stick or a dish.

Depending on the intended application, such as a stick, hardness of the composition may also be considered. The hardness of a composition may, for example, be expressed in gramforce (gf). The composition of the present invention may, for example, have a hardness ranging from 20 gf to 2000 gf, such as from 20 gf to 900 gf, and further such as from 20 gf to 600 gf.

This hardness is measured in one of two ways. A first test for hardness is according to a method of penetrating a probe into the composition and in particular using a texture analyzer (for example TA-XT2i from Rheo) equipped with an ebonite cylinder of height 25 mm and diameter 8 mm. The hardness measurement is carried out at 20° C. at the center of 5 samples of the composition. The cylinder is introduced into each sample of composition at a pre-speed of 2 mm/s and then at a speed of 0.5 mm/s and finally at a post-speed of 2 mm/s, the total displacement being 1 mm. The recorded hardness value is that of the maximum peak observed. The measurement error is ±50 gf.

The second test for hardness is the "cheese wire" method, which involves cutting an 8.1 mm or preferably 12.7 mm in diameter stick composition and measuring its hardness at 20° C. using a DFGHS 2 tensile testing machine from Indelco-Chatillon Co. at a speed of 100 mm/minute. The hardness value from this method is expressed in grams as the shear force required to cut a stick under the above conditions.

According to this method, the hardness of compositions according to the present invention which may be in stick form may, for example, range from 30 gf to 300 gf, such as from 30 gf to 250 gf, for a sample of 8.1 mm in diameter stick, and further such as from 30 gf to 200 gf, and also further such as from 30 gf to 120 gf for a sample of 12.7 mm in diameter stick.

The hardness of the composition of the present invention may be such that the compositions are self-supporting and can easily disintegrate to form a satisfactory deposit on keratin materials. In addition, this hardness may impart good impact strength to the inventive compositions, which may be molded or cast, for example, in stick or dish form.

The skilled artisan may choose to evaluate a composition using at least one of the tests for hardness outlined above based on the application envisaged and the hardness desired. If one obtains an acceptable hardness value, in view of the intended application, from at least one of these hardness tests, the composition falls within preferred embodiments of the invention.

As defined herein, stability is tested by placing the composition in a controlled environment chamber for 8 weeks at 25° C. In this test, the physical condition of the sample is inspected as it is placed in the chamber. The sample is then inspected again at 24 hours, 3 days, 1 week, 2 weeks, 4 weeks and 8 weeks. At each inspection, the sample is examined for abnormalities in the composition such as phase separation if the composition is in the form of an emulsion, bending or leaning if the composition is in stick form, melting, or syneresis (or sweating). The stability is further tested by repeating the 8-week test at 25° C., 37° C., 45° C. and under freeze-thaw conditions. A composition is considered to lack stability if in any of these tests an abnormality that impedes functioning of the composition is observed. The skilled artisan will readily recognize an abnormality that impedes functioning of a composition based on the intended application.

The cosmetic compositions and methods of the present invention can comprise, consist of, or consist essentially of the essential elements and limitations of the invention described herein, as well as any additional or optional ingredients, components, or limitations described herein or otherwise useful in personal care.

Hyperbranched Polyol Compound

According to the present invention, compositions comprising at least one hyperbranched polyol compound are provided.

Preferably, the hyperbranched polyol has a hydroxyl number of at least 15, more preferably of at least 50, more preferably of at least 100, and more preferably of at least about 150. "Hydroxyl number" or "hydroxyl value" which is sometimes also referred to as "acetyl value" is a number which indicates the extent to which a substance may be acetylated; it is the number of milligrams of potassium hydroxide required for neutralization of the acetic acid liberated on saponifying 1 g of acetylated sample.

In accordance with the present invention, "hyperbranched polyol" refers to dendrimers, hyperbranched macromolecules and other dendron-based architectures. Hyperbranched polyols can generally be described as three-dimensional highly branched molecules having a tree-like structure. They are characterized by a great number of end groups, at least two of which are hydroxyl groups. The dendritic or "tree-like" structure preferably shows regular symmetric branching from a central multifunctional core molecule leading to a compact globular or quasi-globular structure with a large number of end groups per molecule. Suitable examples of hyperbranched polyols can be found in U.S. Pat. No.

7,423,104, and U.S. patent applications 2008/0207871 and 2008/0286152, the entire contents of all of which are hereby incorporated by reference.

Other suitable examples include alcohol functional olefinic polymers such as those available from New Phase Technologies. For example, olefinic polymers such as those disclosed in U.S. Pat. No. 7,314,904, the entire contents of which is hereby incorporated by reference, can be used. Thus, for example, a functionalized polyalphaolefin comprising the reaction product of admixing an alpha-olefin monomer having at least 10 carbon atoms and an unsaturated functionalizing compound can be used. Non-functionalized olefins that may be used in accordance with the present invention include, but are not limited to, 1-decene, 1-dodecene, 1-tetradecene, 1-hexadecene, 1-octadecene, 1-eicosene, as well as such commercial mixtures sold as alpha-olefins including those having mainly C10-C13, C20-C24 chain lengths, C24-C28 chain lengths and C30 and higher chain lengths. Examples of commercial alpha olefin admixtures useful with the present invention include ALPHA OLEFIN 30+ from Chevron Phillips and Alpha Olefin Fraction C30+ from Gulf.

Unsaturated functionalizing compounds useful with the present invention include, but are not limited to, carboxylic acids, carboxylic acid esters, amides, ethers, amines, phosphate esters, silanes and alcohols. Examples of such carboxylic acids include, but are not limited to, 5-hexenoic acid, 6-heptenoic acid, 10-undecylenic acid, 9-decenoic acid, oleic acid, and erucic acid. Also useful are esters of these acids with linear or branched-chain alcohols having from about 1 to about 10 carbon atoms, as well as triglycerides containing olefinic unsaturation in the fatty acid portion such as tall oil, fish oils, soybean oil, linseed oil, cottonseed oil and partially hydrogenated products of such oils. Other useful materials include olefinic alcohols such as allyl alcohol, 9-decen-1-ol, 10-undecylenyl alcohol, oleyl alcohol, erucyl alcohol, acetic acid or formic acid esters of these alcohols, C1-C4 alkyl ether derivatives of these alcohols and formamides or acetamides of unsaturated amines such as oleylamine, erucylamine, 10-undecylenylamine and allylamine.

The molar ratio of alpha olefin monomer to unsaturated functionalizing compound useful with the present invention is preferably from about 20:1 to 1:20. Also preferably, the molar ratio of alpha olefin monomer to unsaturated functionalizing compound useful with the present invention is from about 10:1 to 1:10. Most preferably the molar ratio of alpha olefin monomer to unsaturated functionalizing compound useful with the present invention is from about 8:1 to 1:2.

After the polymerization, the functionalized polyalphaolefins of the present invention preferably have a molecular weight, determined using gel permeation chromatography procedure and a polystyrene standard of from about 200 daltons to about 150,000 daltons. Also preferably, the functionalized polyalphaolefins of the present invention have a molecular weight of from about 400 daltons to about 80,000 daltons. Most preferably, the functionalized polyalphaolefins of the present invention have a molecular weight of from about 600 daltons to about 6,000 daltons.

According to preferred embodiments, the alcohol functional olefinic polymer has a dynamic viscosity preferably ranging from 0.1 Pa·s to 100 Pa·s, preferably ranging from 0.1 Pa·s to 50 Pa·s, and preferably ranging from 0.1 Pa·s to 10 Pa·s at room temperature.

A particularly preferred alcohol functional olefinic polymer is C20-C24 olefin/oleyl alcohol available from New Phase Technologies.

With respect to dendrimers, these tend to be exact, monodisperse structures built layerwise (in generations) around a core moiety, with a polymer branching point in every repeating unit. Hyperbranched polymers tend to possess a number of characteristics which are similar to dendrimers but they tend to be polydisperse and contain relatively linear segments off of which a plurality of highly branched segments are grown or attached.

Furthermore, "hyperbranched polymers" refers to polymers comprising at least two, for example three, polymeric branches, forming either the main branch or a secondary branch, and each comprising at least one at least trifunctional branch point, which may be identical or different, and which is able to form at least two at least trifunctional branch points, different from and independent of one another. Each branch point may be, for example, arranged in the interior of at least one chain. The branches may be, for example, connected to one another by a polyfunctional compound.

As used herein, "trifunctional branch point" means the junction point between three polymer branches, of which at least two branches may be different in chemical constitution and/or structure. For example, certain branches may be hydrophilic, i.e. may predominantly contain hydrophilic monomers, and other branches may be hydrophobic, i.e., may predominantly contain hydrophobic monomers. Further branches may additionally form a random polymer or a block polymer.

As used herein, "at least trifunctional branch" means the junction points between at least three polymeric branches, for example n polymeric branches, of which n−1 branches at least are different in chemical constitution and/or structure.

As used herein, "chain interior" means the atoms situated within the polymeric chain, to the exclusion of the atoms forming the two ends of this chain.

As used herein, "main branch" means the branch or polymeric sequence comprising the greatest percentage by weight of monomer(s).

Branches which are not main branches are called "secondary branches".

According to particularly preferred embodiments of the present invention, the hyperbranched polyol comprises a hydrophobic chain interior. Preferably, the chain interior comprises one or more hydrocarbon groups, one or more silicon-based groups, or mixtures thereof. Particularly preferred chain interiors comprise olefinic polymers or copolymers and/or silicone polymers or copolymers.

Suitable olefinic monomers include, but are not limited to, compounds having from about 2 to about 30 carbon atoms per molecule and having at least one olefinic double bond which are acyclic, cyclic, polycyclic, terminal α, internal, linear, branched, substituted, unsubstituted, functionalized, and/or non-functionalized. For example, suitable monomers include ethylene, propylene, 1-butene, 2-butene, 3-methyl-1-butene, and isobutylene.

Suitable silicone groups for inclusion into the interior chain include, but are not limited to, M, D, T, and/or Q groups in accordance with commonly used silicon-related terminology (M=monovalent; D=divalent; T=trivalent; and Q=quadvalent). Particularly preferred monomers are "D" groups such as dimethicone or substituted dimethicone groups. Such groups can help form, for example, suitable dimethicone copolyols in accordance with the present invention.

According to preferred embodiments, the at least one hyperbranched polyol is present in the composition of the present invention in an amount ranging from about 1 to less than 30% by weight, more preferably from about 7 to about 27% by weight, more preferably from about 15 to about 25% by weight, based on the total weight of the composition, including all ranges and subranges within these ranges.

Acrylic Film Forming Agents

According to the present invention, compositions comprising at least one at least one film forming agent (film former) are provided. Acceptable film forming agents are known in the art and include, but are not limited to, those disclosed in U.S. patent application publication no. 2004/0170586, the entire contents of which is hereby incorporated by reference.

Particularly preferred film forming agents are acrylic film forming agents. "Acrylic film formers" as used herein refers to polymers that are film forming agents and which are based upon one or more (meth)acrylic acid (and corresponding (meth)acrylate) monomers or similar monomers.

Non-limiting representative examples of such film forming agents include copolymers containing at least one apolar monomer, at least one olefinically unsaturated monomer, and at least one vinylically functionalized monomer.

For the apolar monomers, acrylic monomers which comprise acrylic and methacrylic esters with alkyl groups composed of 4 to 14 C atoms, preferably 4 to 9 C atoms are preferred. Examples of monomers of this kind are n-butyl acrylate, n-butyl methacrylate, n-pentyl acrylate, n-pentyl methacrylate, n-amyl acrylate, n-hexyl acrylate, hexyl methacrylate, n-heptyl acrylate, n-octyl acrylate, n-octyl methacrylate, n-nonyl acrylate, isobutyl acrylate, isooctyl acrylate, isooctyl methacrylate, and their branched isomers, such as, for example, 2-ethylhexyl acrylate, 2-ethylhexyl methacrylate.

For olefinically unsaturated monomers, it is preferred to use monomers having functional groups selected from hydroxyl, carboxyl, sulphonic acid groups, phosphonic acid groups, acid anhydrides, epoxides, and amines. Particularly preferred examples of olefinically unsaturated monomers include acrylic acid, methacrylic acid, itaconic acid, maleic acid, fumaric acid, crotonic acid, aconitic acid, dimethylacrylic acid, beta-acryloyloxypropionic acid, trichloracrylic acid, vinylacetic acid, vinylphosphonic acid, itaconic acid, maleic anhydride, hydroxyethyl acrylate, hydroxypropyl acrylate, hydroxyethyl methacrylate, hydroxypropyl methacrylate, 6-hydroxyhexyl methacrylate, allyl alcohol, glycidyl acrylate, glycidyl methacrylate.

For vinylically functionalized compounds, preferred monomers include monomers which are copolymerizable with one or both of the previously discussed monomers and include, for example, methyl acrylate, ethyl acrylate, propyl acrylate, methyl methacrylate, ethyl methacrylate, benzyl acrylate, benzyl methacrylate, sec-butyl acrylate, tert-butyl acrylate, phenyl acrylate, phenyl methacrylate, isobornyl acrylate, isobornyl methacrylate, tert-butylphenyl acrylate, tert-butylphenyl methacrylate, dodecyl methacrylate, isodecyl acrylate, lauryl acrylate, n-undecyl acrylate, stearyl acrylate, tridecyl acrylate, behenyl acrylate, cyclohexyl methacrylate, cyclopentyl methacrylate, phenoxyethyl acrylate, phenoxyethyl methacrylate, 2-butoxyethyl methacrylate, 2-butoxyethyl acrylate, 3,3,5-trimethylcyclohexyl acrylate, 3,5-dimethyladamantyl acrylate, 4-cumylphenyl methacrylate, cyanoethyl acrylate, cyanoethyl methacrylate, 4-biphenyl acrylate, 4-biphenyl methacrylate, 2-naphthyl acrylate, 2-naphthyl methacrylate, tetrahydrofurfuryl acrylate, diethylaminoethyl acrylate, diethylaminoethyl methacrylate, dimethylaminoethyl acrylate, dimethylaminoethyl methacrylate, 2-butoxyethyl acrylate, 2-butoxyethyl methacrylate, methyl 3-methoxyacrylate, 3-methoxybutyl acrylate, phenoxyethyl acrylate, phenoxyethyl methacrylate, 2-phenoxyethyl methacrylate, butyldiglycol methacrylate, ethylene glycol acrylate, ethylene glycol monomethylacrylate, methoxy-polyethylene glycol methacrylate 350, methoxy-polyethylene glycol methacrylate 500, propylene glycol monomethacrylate, butoxydiethylene glycol methacrylate, ethoxytriethylene glycol methacrylate, octafluoropentyl acrylate, octafluoropentyl methacrylate, 2,2,2-trifluoroethyl methacrylate, 1,1,1,3,3,3-hexafluoroisopropyl acrylate, 1,1,1,3,3,3-hexafluoroisopropyl methacrylate, 2,2,3,3,3-pentafluoropropyl methacrylate, 2,2,3,4,4,4-hexafluorobutyl methacrylate, 2,2,3,3,4,4,4-heptafluorobutyl acrylate, 2,2,3,3,4,4,4-heptafluorobutyl methacrylate, 2,2,3,3,4,4,5,5,6,6,7,7,8,8,8-pentadecafluorooctyl methacrylate, dimethylaminopropylacrylamide, dimethylaminopropylmethacrylamide, N-(1-methylundecyl)acrylamide, N-(n-butoxymethyl)acrylamide, N-(butoxymethyl)methacrylamide, N-(ethoxymethyl)acrylamide, N-(n-octadecyl)acrylamide, and also N,N-dialkyl-substituted amides, such as, for example, N,N-dimethylacrylamide, N,N-dimethylmethacrylamide, N-benzylacrylamides, N-isopropylacrylamide, N-tert-butylacrylamide, N-tert-octylacrylamide, N-methylolacrylamide, N-methylolmethacrylamide, acrylonitrile, methacrylonitrile, vinyl ethers, such as vinyl methyl ether, ethyl vinyl ether, vinyl isobutyl ether, vinyl esters, such as vinyl acetate, vinyl chloride, vinyl halides, vinylidene chloride, vinylidene halide, vinylpyridine, 4-vinylpyridine, N-vinylphthalimide, N-vinyllactam, N-vinylpyrrolidone, styrene, a- and p-methylstyrene, a-butylstyrene, 4-n-butylstyrene, 4-n-decylstyrene, 3,4-dimethoxystyrene, macromonomers such as 2-polystyrene-ethyl methacrylate (molecular weight Mw of 4000 to 13 000 g/mol), poly(methyl methacrylate) ethyl methacrylate (Mw of 2000 to 8000 g/mol).

A particularly preferred film former is a copolymer of acrylic acid, isobutyl acrylate and isobornyl acetate such as that sold under the names Pseudoblock (Chimex) and Synamer-3.

According to preferred embodiments, the film former is present in the composition in an amount ranging from 0.1% to 30% by weight relative to the total weight of the composition. Preferably, the film former is present in an amount ranging from 1% to 20% by weight relative to the total weight of the composition, and more preferably from 2% to 10%, including all ranges and subranges therebetween. One of ordinary skill in the art will recognize that the film former of the present invention may be commercially available, and may come from suppliers in the form of a dilute solution. The amounts of the film former disclosed herein therefore reflect the weight percent of active material.

According to preferred embodiments, the hyperbranched polyol and the film forming agent are present in the compositions of the present invention in a weight ratio of between 10:1 and 1:1, preferably between 7:1 and 1.5:1, and preferably between 5:1 and 2:1, including all ranges and subranges therebetween.

Tackifiers

According to the present invention, compositions comprising at least one tackifier are provided. In accordance with the present invention, a substance is described as a tackifier if, by adding it to sufficient block copolymer, the resulting composition has the properties of a pressure sensitive adhesive. However, for purposes of the present invention, "tackifier" in the compositions of the present invention do not have to possess tackifying properties, particularly if little or no block copolymer is present in the compositions. Rather, according to preferred embodiments, the tackifier possesses film forming properties in the compositions of the present invention. Thus, "tackifier" is meant to describe particular compounds, but not necessarily properties of such compounds in the compositions of the present invention.

In general, tackifiers can be divided into four different families in terms of their chemistry: hydrocarbon resins, terpenes, amorphous (i.e. non-crystalline) rosins, rosin esters and their derivatives, and pure monomer resins. These tackifiers are characterized by their compatibility with at least one segment of the block copolymer. By the term "compatible", it is meant, for example, that when the block copolymer and tackifier are mixed, the combination of at least one segment of the block copolymer with the tackifier forms a polymer blend having a single glass transition temperature $T_g$ which may be measured by DMA, DSC or neutron light scattering.

The compatibility of the block copolymer and the tackifier may also be defined in terms of solubility parameters. The solubility parameter δ according to the Hansen solubility space is defined in the article "*Solubility Parameter Values*" by Eric A. Grulke in the work "*Polymer Handbook*" 3$^{rd}$ edition, Chapter VII, pages 519-559, the entire content of which is hereby incorporated by reference, by the relationship:

$$\delta = (d_D^2 + d_P^2 + d_H^2)^{1/2},$$

in which:
  $d_D$ characterizes the London dispersion forces resulting from the formation of dipoles induced during molecular impacts,
  $d_P$ characterizes the forces of Debye interactions between permanent dipoles,
  $d_H$ characterizes the forces of specific interactions (hydrogen bond, acid/base or donor/acceptor type and the like). The definition of the solvents in the three-dimensional solubility space according to Hansen is given in the article by C. M. Hansen: "*The three-dimensional solubility parameters*" J. Paint Technol., 39, 105 (1967), the entire content of which is hereby incorporated by reference.

The at least one tackifier used in the present invention preferably has a solubility parameter corresponding to 6 and the block copolymer preferably has at least one segment whose solubility parameter corresponds to δ±2, preferably δ±1.7, more preferably δ±1.5, more preferably δ±1.3, more preferably δ±1.0, more preferably δ±0.7, more preferably δ±0.5, and more preferably δ±0.3.

Examples of suitable tackifiers, include, but are not limited to, aliphatic hydrocarbon resins, aromatic modified aliphatic hydrocarbon resins, hydrogenated polycyclopentadiene resins, polycyclopentadiene resins, gum rosins, gum rosin esters, wood rosins, wood rosin esters, tall oil rosins, tall oil rosin esters, polyterpenes, aromatic modified polyterpenes, terpene phenolics, aromatic modified hydrogenated polycyclopentadiene resins, hydrogenated aliphatic resin, hydrogenated aliphatic aromatic resins, hydrogenated terpenes and modified terpenes, hydrogenated rosin acids, hydrogenated rosin esters, polyisoprene, partially or fully hydrogenated polyisoprene, polybutenediene, partially or fully hydrogenated polybutenediene, and the like. As is evidenced by some of the cited examples, the tackifier may be fully or partially hydrogenated. The tackifier may also be non-polar, where "non-polar" means that the tackifier is substantially free of monomers having polar groups. Preferably, polar groups are not present; however, if they are present, they are preferably present in an amount of up to about 5% by weight, preferably up to about 2% by weight, and more preferably up to about 0.5% by weight.

In preferred embodiments, the tackifier may have a softening point (Ring and Ball, as measured by ASTM E-28) of about 80° C. to about 150° C., preferably about 100° C. to about 130° C. In other preferred embodiments, the tackifier may be liquid and have an R and B softening point of between about −70° C. and about 70° C.

According to preferred embodiments, the tackifiers are hydrogenated hydrocarbon resins such as a hydrogenated styrene/methyl styrene/indene copolymer e.g., styrene/methyl styrene/indene copolymers which include R1090, R1100, R7100, S1100, and S5100, all which are commercially available from Eastman Chemical under the trade name Regalite®. In other embodiments, aliphatic or aromatic hydrocarbon-based tackifying resins, for instance the resins sold under the name "Piccotac" and "Hercotac" from Hercules or "Escorez" from Exxon, may also be used. It is also to be understood that mixtures of tackifiers may also be employed without departing from the spirit of the invention.

A particularly preferred tackifier for use in the present invention is a hydrogenated hydrocarbon resin such as, for example, a hydrogenated styrene/methyl styrene/indene copolymer, commercially available from Eastman under the tradename Regalite® R1100.

In the composition of the present invention, the tackifier(s) are preferably present in an amount of from about 0.1 to about 60 percent by weight, more preferably from 1 to 40 percent by weight, more preferably from 1 to 20 percent by weight and most preferably from 1 to 10 percent by weight of the total weight of the composition, including all ranges and subranges therebetween Block Copolymer According to preferred embodiments of the present invention, compositions can optionally further comprise at least one block copolymer. The block copolymers of the present invention are characterized by the presence of at least one "hard" segment, and at least one "soft" segment. Aside from their compositional nature, the hard and soft segments of the block copolymers of the present invention are defined in terms of their respective glass transition temperatures, "$T_g$". More particularly, the hard segment has a $T_g$ of about 50° C. or more, whereas the soft segment has a $T_g$ of about 20° C. or less. The glass transition temperature $T_g$ for the hard block can range from about 50° C. to about 150° C.; about 60° C. to about 125° C.; about 70° C. to about 120° C.; or about 80° C. to about 110° C. The glass transition temperature $T_g$ for the soft segment of the block copolymer can range from about 20° C. to about −150° C.; about 0° C. to about −135° C.; about −10° C. to about −125° C.; and about −25° C. to about −100° C. A more in depth explanation can be found in U.S. Pat. Nos. 5,294,438 and 6,403,070, the entire contents of which are hereby incorporated by reference.

One type of block copolymer which may be employed in the compositions of the present invention is a thermoplastic elastomer. The hard segments of the thermoplastic elastomer typically comprise vinyl monomers in varying amounts. Examples of suitable vinyl monomers include, but are not limited to, styrene, methacrylate, acrylate, vinyl ester, vinyl ether, vinyl acetate, and the like.

The soft segments of the thermoplastic elastomer typically comprise olefin polymers and/or copolymers which may be saturated, unsaturated, or combinations thereof. Suitable olefin copolymers may include, but are not limited to, ethylene/propylene copolymers, ethylene/butylene copolymers, propylene/butylene copolymers, polybutylene, polyisoprene, polymers of hydrogenated butanes and isoprenes, and mixtures thereof.

Thermoplastic elastomers useful in the present invention include block copolymers e.g., di-block, tri-block, multi-block, radial and star block copolymers, and mixtures and blends thereof. A di-block thermoplastic elastomer is usually defined as an A-B type or a hard segment (A) followed by a soft segment (B) in sequence. A tri-block is usually defined as an A-B-A type copolymer or a ratio of one hard, one soft, and one hard segment. Multi-block or radial block or star block thermoplastic elastomers usually contain any combination of hard and soft segments, provided that the elastomers possess both hard and soft characteristics.

In preferred embodiments, the thermoplastic elastomer of the present invention may be chosen from the class of Kraton™ rubbers (Shell Chemical Company) or from similar thermoplastic elastomers. Kraton™ rubbers are thermoplastic elastomers in which the polymer chains comprise a di-block, tri-block, multi-block or radial or star block configuration or numerous mixtures thereof. The Kraton™ tri-block rubbers have polystyrene (hard) segments on each end of a rubber (soft) segment, while the Kraton™ di-block rubbers have a polystyrene (hard) segment attached to a rubber (soft) segment. The Kraton™ radial or star configuration may be a four-point or other multipoint star made of rubber with a polystyrene segment attached to each end of a rubber segment. The configuration of each of the Kraton™ rubbers forms separate polystyrene and rubber domains.

Each molecule of Kraton™ rubber is said to comprise block segments of styrene monomer units and rubber monomer and/or co-monomer units. The most common structure for the Kraton™ triblock copolymer is the linear A-B-A block type styrene-butadiene-styrene, styrene-isoprene-styrene, styrene-ethylenepropylene-styrene, or styrene-ethylenebutylene-styrene. The Kraton™ di-block is preferably the AB block type such as styrene-ethylenepropylene, styrene-ethylenebutylene, styrene-butadiene, or styrene-isoprene. The Kraton™ rubber configuration is well known in the art and any block copolymer elastomer with a similar configuration is within the practice of the invention. Other block copolymers are sold under the tradename Septon (which represent elastomers known as SEEPS, sold by Kurary, Co., Ltd) and those sold by Exxon Dow under the tradename Vector™.

Other thermoplastic elastomers useful in the present invention include those block copolymer elastomers comprising a styrene-butylene/ethylene-styrene copolymer (tri-block), an ethylene/propylene-styrene copolymer (radial or star block) or a mixture or blend of the two. (Some manufacturers refer to block copolymers as hydrogenated block copolymers, e.g. hydrogenated styrene-butylene/ethylene-styrene copolymer (tri-block)).

The amounts of the block (co)polymer or (co)polymers, as well as their structure (di-block, tri-block, etc.), affect the nature of the thermoplastic elastomer, including its gelled form, which may range from fragile to soft/flexible to firm. For instance, soft gels contain relatively high amounts of soft segments, and firm gels contain relatively high amounts of hard segments. The overall properties of the composition may also be affected by including more than one such block copolymer e.g., including a mixture of copolymers. For example, the presence of tri-block copolymers enhances the integrity of the film formed. The gel may also be transparent, translucent or opaque, depending upon the other cosmetically acceptable ingredients added, as described herein.

It is preferred that the styrene content of the block copolymer be less than 30% by weight, preferably less than 25% by weight, and more preferably less than 20% by weight, based on the weight of the block copolymer. This is because of the tendency of block copolymers having a styrene content of greater than 30% by weight to harden/gel in conventional carrier systems. However, in the event that a block copolymer having a styrene content of greater than 30% by weight is used, it may be necessary to also employ a co-solvent or functional ingredient capable of dissolving a styrene block in an amount effective to control the hardening/gelling of the styrene-containing elastomer in the cosmetic composition.

A particularly preferred block copolymer for use in the present invention is a combination of di-block and tri-block copolymers of styrene-ethylene/butylene-styrene, commercially available from Shell Chemical Company under trade name Kraton G1657M. It should be noted, however, that any thermoplastic elastomer of the block copolymer type having at least one soft and at least one hard segment may be used without departing from the spirit of the invention.

The block copolymer will preferably have a solubility parameter, relative to the tackifier component, of $\delta\pm2$, more preferably $\delta\pm1.7$, more preferably $\delta\pm1.5$, more preferably $\delta\pm1.3$, more preferably $\delta\pm1.0$, more preferably $\delta\pm0.7$, more preferably $\delta\pm0.5$, and more preferably $\delta\pm0.3$.

If present in the composition of the present invention, the block copolymer(s) are preferably present in an amount of from about 0.1 to about 50 percent by weight, more preferably from 0.3 to 10 percent by weight, more preferably from 0.5 to 4 percent by weight of the total weight of the composition, including all ranges and subranges therebetween.

Oil Phase

According to the present invention, compositions comprising at least one fatty substance are provided. Suitable fatty substances include oil(s) and/or wax(es). "Oil" means any non-aqueous medium which is liquid at ambient temperature (25° C.) and atmospheric pressure (760 mm Hg). A "wax" for the purposes of the present disclosure is a lipophilic fatty compound that is solid at ambient temperature (25° C.) and changes from the solid to the liquid state reversibly, having a melting temperature of more than 30° C. and, for example, more than 45° C., which can be as high as 150° C., a hardness of more than 0.5 MPa at ambient temperature, and an anisotropic crystalline organization in the solid state. By taking the wax to its melting temperature, it is possible to use wax(es) by themselves as carriers and/or it is possible to make wax(es) miscible with the oils to form a microscopically homogeneous mixture.

Suitable oils include volatile and/or non-volatile oils. Such oils can be any acceptable oil including but not limited to silicone oils and/or hydrocarbon oils.

According to certain embodiments, the composition of the present invention preferably comprise one or more volatile silicone oils. Examples of such volatile silicone oils include linear or cyclic silicone oils having a viscosity at room temperature less than or equal to 6 cSt and having from 2 to 7 silicon atoms, these silicones being optionally substituted with alkyl or alkoxy groups of 1 to 10 carbon atoms. Specific oils that may be used in the invention include octamethyltetrasiloxane, decamethylcyclopentasiloxane, dodecamethylcyclohexasiloxane, heptamethyloctyltrisiloxane, hexamethyldisiloxane, decamethyltetrasiloxane, dodecamethylpentasiloxane and their mixtures. Other volatile oils which may be used include KF 96A of 6 cSt viscosity, a commercial product from Shin Etsu having a flash point of 94° C. Preferably, the volatile silicone oils have a flash point of at least 40° C.

Non-limiting examples of volatile silicone oils are listed in Table 1 below.

TABLE 1

| Compound | Flash Point (° C.) | Viscosity (cSt) |
|---|---|---|
| Octyltrimethicone | 93 | 1.2 |
| Hexyltrimethicone | 79 | 1.2 |

TABLE 1-continued

| Compound | Flash Point (° C.) | Viscosity (cSt) |
|---|---|---|
| Decamethylcyclopentasiloxane (cyclopentasiloxane or D5) | 72 | 4.2 |
| Octamethylcyclotetrasiloxane (cyclotetradimethylsiloxane or D4) | 55 | 2.5 |
| Dodecamethylcyclohexasiloxane (D6) | 93 | 7 |
| Decamethyltetrasiloxane(L4) | 63 | 1.7 |
| KF-96 A from Shin Etsu | 94 | 6 |
| PDMS (polydimethylsiloxane) DC 200 (1.5 cSt) from Dow Corning | 56 | 1.5 |
| PDMS DC 200 (2 cSt) from Dow Corning | 87 | 2 |

Further, a volatile linear silicone oil may be employed in the present invention. Suitable volatile linear silicone oils include those described in U.S. Pat. No. 6,338,839 and WO03/042221, the contents of which are incorporated herein by reference. In one embodiment the volatile linear silicone oil is decamethyltetrasiloxane. In another embodiment, the decamethyltetrasiloxane is further combined with another solvent that is more volatile than decamethyltetrasiloxane.

According to other embodiments, the composition of the present invention preferably comprises one or more non-silicone volatile oils and may be selected from volatile hydrocarbon oils, volatile esters and volatile ethers. Examples of such volatile non-silicone oils include, but are not limited to, volatile hydrocarbon oils having from 8 to 16 carbon atoms and their mixtures and in particular branched $C_8$ to $C_{16}$ alkanes such as $C_8$ to $C_{16}$ isoalkanes (also known as isoparaffins), isohexacecane, isododecane, isodecane, and for example, the oils sold under the trade names of Isopar or Permethyl. Preferably, the volatile non-silicone oils have a flash point of at least 40° C.

Non-limiting examples of volatile non-silicone volatile oils are given in Table 2 below.

TABLE 2

| Compound | Flash Point (° C.) |
|---|---|
| Isododecane | 43 |
| Propylene glycol n-butyl ether | 60 |
| Ethyl 3-ethoxypropionate | 58 |
| Propylene glycol methylether acetate | 46 |
| Isopar L (isoparaffin $C_{11}$-$C_{13}$) | 62 |
| Isopar H (isoparaffin $C_{11}$-$C_{12}$) | 56 |

The volatility of the solvents/oils can be determined using the evaporation speed as set forth in U.S. Pat. No. 6,338,839, the contents of which are incorporated by reference herein.

According to other embodiments of the present invention, the composition comprises at least one non-volatile oil. Examples of non-volatile oils that may be used in the present invention include, but are not limited to, polar oils such as:
  hydrocarbon-based plant oils with a high triglyceride content consisting of fatty acid esters of glycerol, the fatty acids of which may have varied chain lengths, these chains possibly being linear or branched, and saturated or unsaturated; these oils are especially wheat germ oil, corn oil, sunflower oil, karite butter, castor oil, sweet almond oil, macadamia oil, apricot oil, soybean oil, rapeseed oil, cottonseed oil, alfalfa oil, poppy oil, pumpkin oil, sesame seed oil, marrow oil, avocado oil, hazelnut oil, grape seed oil, blackcurrant seed oil, evening primrose oil, millet oil, barley oil, quinoa oil, olive oil, rye oil, safflower oil, candlenut oil, passion flower oil or musk rose oil; or caprylic/capric acid triglycerides, for instance those sold by the company Stearineries Dubois or those sold under the names Miglyol 810, 812 and 818 by the company Dynamit Nobel;
  synthetic oils or esters of formula $R_5COOR_6$ in which $R_5$ represents a linear or branched higher fatty acid residue containing from 1 to 40 carbon atoms, including from 7 to 19 carbon atoms, and $R_6$ represents a branched hydrocarbon-based chain containing from 1 to 40 carbon atoms, including from 3 to 20 carbon atoms, with $R_6+R_7 \geq 10$, such as, for example, Purcellin oil (cetostearyl octanoate), isononyl isononanoate, octyldodecyl neopentanoate, $C_{12}$ to $C_{15}$ alkyl benzoate, isopropyl myristate, 2-ethylhexyl palmitate, and octanoates, decanoates or ricinoleates of alcohols or of polyalcohols; hydroxylated esters, for instance isostearyl lactate or diisostearyl malate; and pentaerythritol esters;
  synthetic ethers containing from 10 to 40 carbon atoms;
  $C_8$ to $C_{26}$ fatty alcohols, for instance oleyl alcohol, cetyl alcohol, stearyl alcohol, and cetearly alcohol; and
  mixtures thereof.

Further, examples of non-volatile oils that may be used in the present invention include, but are not limited to, non-polar oils such as branched and unbranched hydrocarbons and hydrocarbon waxes including polyolefins, in particular Vaseline (petrolatum), paraffin oil, squalene, squalane, hydrogenated polyisobutene, hydrogenated polydecene, polybutene, mineral oil, pentahydrosqualene, and mixtures thereof.

According to preferred embodiments of the present invention, the at least oil is a high viscosity oil which is a silicone oil and/or a hydrocarbon oil.

Suitable examples of such silicone oils include, but are not limited to, non-volatile silicone fluids such as, for example, polyalkyl (aryl) siloxanes. Suitable polyalkyl siloxanes include, but are not limited to, polydimethyl siloxanes, which have the CTFA designation dimethicone, polydiethyl siloxane, phenyl trimethicone, trimethyl pentaphenyl trisiloxane, phenyldimethicone, phenyltrimethylsiloxydiphenylsiloxane, diphenyldimethicone, and diphenylmethyldiphenyltrisiloxane and those siloxanes disclosed in U.S. patent application publication no. 2004/0126350, the entire disclosure of which is hereby incorporated by reference. Specific examples of suitable high viscosity silicone oils include, but are not limited to, 15 M 30 from PCR (500 cSt) or Belsil PDM 1000 (1 000 cSt) from Wacker and Dow Corning 200 (350 cSt) (the values in parenthesis represent viscosities at 25° C.).

Suitable examples of such hydrocarbon oils include, but are not limited to, fluids having a molecular mass of more than 500 g/mol, for example more than 600 g/mol, and for example more than 650 g/mol. By "hydrocarbon" compound, it is meant a compound comprising principally atoms of carbon and hydrogen and optionally one or more functional groups chosen from hydroxyl, ester, ether and carboxyl functions. These compounds are, according to one aspect, devoid of —Si—O— groups. Suitable examples of hydrocarbon fluids include, but are not limited to polybutylenes, such as Indopol H-100 (of molar mass or MM=965 g/mol), Indopol H-300 (MM=1 340 g/mol), and Indopol H-1500 (MM=2 160 g/mol), which are sold or manufactured by Amoco; hydrogenated polyisobutylenes, such as Panalane H-300 E, sold or manufactured by Amoco (M=1 340 g/mol), Viseal 20000 sold or manufactured by Synteal (MM=6 000 g/mol), and Rewopal PIB 1000, sold or manufactured by Witco (MM=1 000 g/mol); polydecenes and hydrogenated polydecenes, such as Puresyn 10 (MM=723 g/mol) and Puresyn 150 (MM=9 200 g/mol) sold or manufactured by Mobil Chemicals; esters such as linear fatty acid esters having a total carbon number ranging from 30 to 70, such as pentaerythrityl tetrapelargonate (MM=697.05 g/mol); hydroxy esters, such as diisostearyl malate (MM=639 g/mol); aromatic esters such as tridecyl trimellitate (MM=757.19 g/mol); esters of C24-C28 branched fatty acids or fatty alcohols, such as those described in EP-A-0 955 039, for example triisocetyl citrate (MM=856 g/mol), pentaerythrityl tetraisononanoate (MM=697.05 g/mol), glyceryl triisostearate (MM=891.51 g/mol), glyceryl 2-tridecyltetradecanoate (MM=1 143.98 g/mol), pentaerythrityl tetraisostearate (MM=1 202.02 g/mol), poly-2-glyceryl tetraisostearate (MM=1 232.04 g/mol) and pentaerythrityl 2-tetradecyltetradecanoate (MM=1 538.66 g/mol); and mixtures thereof. Suitable ester oils can also be described according to formula $R_1COOR_2$ in which $R_1$ represents a linear or branched higher fatty acid residue containing from 1 to 40 carbon atoms, including from 7 to 19 carbon atoms, and $R_2$ represents a branched hydrocarbon-based chain containing from 1 to 40 carbon atoms, including from 3 to 20 carbon atoms, with $R_1+R_2 \geq 10$, such as, for example, Purcellin oil (cetostearyl octanoate), isononyl isononanoate, $C_{12}$ to $C_{15}$ alkyl benzoate, isopropyl myristate, 2-ethylhexyl palmitate, and octanoates, decanoates or ricinoleates of alcohols or of polyalcohols; hydroxylated esters, for instance isostearyl lactate or diisostearyl malate; and pentaerythritol esters. A particularly preferred ester is diisostearyl malate.

According to preferred embodiments, the at least one oil is present in the compositions of the present invention in an amount ranging from about 5 to about 60% by weight, more preferably from about 10 to about 50% by weight, and most preferably from about 15 to about 35% by weight, based on the total weight of the composition, including all ranges and subranges within these ranges.

According to preferred embodiments of the present invention, the compositions of the present invention comprise at least one wax. Suitable examples of waxes that can be used in accordance with the present disclosure include those generally used in the cosmetics field: they include those of natural origin, such as beeswax, carnauba wax, candelilla wax, ouricoury wax, Japan wax, cork fibre wax or sugar cane wax, rice wax, montan wax, paraffin wax, lignite wax or microcrystalline wax, ceresin or ozokerite, and hydrogenated oils such as hydrogenated castor oil or jojoba oil; synthetic waxes such as the polyethylene waxes obtained from the polymerization or copolymerization of ethylene, and Fischer-Tropsch waxes, or else esters of fatty acids, such as octacosanyl stearate, glycerides which are concrete at 30° C., for example at 45° C., silicone waxes, such as alkyl- or alkoxydimethicones having an alkyl or alkoxy chain ranging from 10 to 45 carbon atoms, poly(di)methylsiloxane esters which are solid at 30° C. and whose ester chain comprising at least 10 carbon atoms, or else di(1,1,1-trimethylolpropane) tetrastearate, which is sold or manufactured by Heterene under the name HEST 2T-4S, and mixtures thereof.

If present, the wax or waxes may be present in an amount ranging from 0.1 to 50% by weight relative to the total weight of the composition, for example from 1 to 30%, and for example from 3 to 25%, including all ranges and subranges therebetween.

Coloring Agents

According to preferred embodiments of the present invention, compositions further comprising at least one coloring agent are provided. Preferably, such colored compositions can be cosmetic compositions such as, for example, lip compositions (for example, lipstick or liquid lip colors), mascaras, nail polish or foundations.

According to this embodiment, the at least one coloring agent is preferably chosen from pigments, dyes, such as liposoluble dyes, nacreous pigments, and pearling agents.

Representative liposoluble dyes which may be used according to the present invention include Sudan Red, DC Red 17, DC Green 6, β-carotene, soybean oil, Sudan Brown, DC Yellow 11, DC Violet 2, DC Orange 5, annatto, and quinoline yellow. The liposoluble dyes, when present, generally have a concentration ranging up to 20% by weight of the total weight of the composition, such as from 0.0001% to 6%, including all ranges and subranges therebetween.

The nacreous pigments which may be used according to the present invention may be chosen from white nacreous pigments such as mica coated with titanium or with bismuth oxychloride, colored nacreous pigments such as titanium mica with iron oxides, titanium mica with ferric blue or chromium oxide, titanium mica with an organic pigment chosen from those mentioned above, and nacreous pigments based on bismuth oxychloride. The nacreous pigments, if present, be present in the composition in a concentration ranging up to 50% by weight of the total weight of the composition, such as from 0.1% to 20%, preferably from 0.1% to 15%, including all ranges and subranges therebetween.

The pigments, which may be used according to the present invention, may be chosen from white, colored, inorganic, organic, polymeric, nonpolymeric, coated and uncoated pigments. Representative examples of mineral pigments include titanium dioxide, optionally surface-treated, zirconium oxide, zinc oxide, cerium oxide, iron oxides, chromium oxides, manganese violet, ultramarine blue, chromium hydrate, and ferric blue. Representative examples of organic pigments include carbon black, pigments of D & C type, and lakes based on cochineal carmine, barium, strontium, calcium, and aluminum.

If present, the pigments may be present in the composition in a concentration ranging up to 50% by weight of the total weight of the composition, such as from 0.5% to 40%, and further such as from 2% to 30%, including all ranges and subranges therebetween. In the case of certain products, the pigments, including nacreous pigments, may, for example, represent up to 50% by weight of the composition.

Additional Additives

The composition of the invention can also comprise any additive usually used in the field under consideration. For example, dispersants such as poly(12-hydroxystearic acid), antioxidants, film forming agents, essential oils, sunscreens, preserving agents, fragrances, fillers, neutralizing agents, cosmetic and dermatological active agents such as, for example, emollients, moisturizers, vitamins, essential fatty acids, surfactants, silicone elastomers, pasty compounds, viscosity increasing agents such as waxes or liposoluble/lipodispersible polymers, and mixtures thereof can be added. A non-exhaustive listing of such ingredients can be found in U.S. patent application publication no. 2004/0170586, the entire contents of which is hereby incorporated by reference. Further examples of suitable additional components can be found in the other references which have been incorporated by reference in this application. Still further examples of such additional ingredients may be found in the *International Cosmetic Ingredient Dictionary and Handbook* ($9^{th}$ ed. 2002).

A person skilled in the art will take care to select the optional additional additives and/or the amount thereof such that the advantageous properties of the composition according to the invention are not, or are not substantially, adversely affected by the envisaged addition.

These substances may be selected variously by the person skilled in the art in order to prepare a composition which has the desired properties, for example, consistency or texture.

These additives may be present in the composition in a proportion from 0% to 99% (such as from 0.01% to 90%)

relative to the total weight of the composition and further such as from 0.1% to 50% (if present), including all ranges and subranges therebetween.

Needless to say, the composition of the invention should be cosmetically or dermatologically acceptable, i.e., it should contain a non-toxic physiologically acceptable medium and should be able to be applied to the eyelashes of human beings.

According to preferred embodiments of the present invention, methods of treating, caring for and/or making up keratinous material such as skin, lips, eyes and eyelashes by applying compositions of the present invention to the keratinous material in an amount sufficient to treat, care for and/or make up the keratinous material are provided. Preferably, "making up" the keratin material includes applying at least one coloring agent to the keratin material in an amount sufficient to provide color to the keratin material.

According to yet other preferred embodiments, methods of enhancing the appearance of keratinous material by applying compositions of the present invention to the keratinous material in an amount sufficient to enhance the appearance of the keratinous material are provided.

In accordance with the preceding preferred embodiments, the compositions of the present invention comprising at least one hyperbranched polyol and at least one acrylic film former are applied topically to the desired area of the keratin material in an amount sufficient to treat, care for and/or make up the keratinous material, to cover or hide defects associated with keratinous material, skin imperfections or discolorations, or to enhance the appearance of keratinous material. The compositions may be applied to the desired area as needed, preferably once or twice daily, more preferably once daily and then preferably allowed to dry before subjecting to contact such as with clothing or other objects (for example, a glass or a topcoat). Preferably, the composition is allowed to dry for about 1 minute or less, more preferably for about 45 seconds or less. The composition is preferably applied to the desired area that is dry or has been dried prior to application, or to which a basecoat has been previously applied.

According to a preferred embodiment of the present invention, compositions having improved cosmetic properties such as, for example, improved feel upon application (for example, texture, reduced drag, spreadability, and/or reduced tackiness), improved shine (initial shine after application and shine 1 hour after application), increased anti-smudging properties and/or increased long wear properties are provided.

According to other embodiments of the present invention, methods of improving the anti-smudging, transfer-resistance, adherence, shine (initial shine after application and shine 1 hour after application) and/or long wear properties of a composition, comprising adding at least one hyperbranched polyol and at least one acrylic film former to the composition are provided.

According to further embodiments of the present invention, methods of improving the feel or texture of a composition, preferably a makeup compositions such as a foundation or lip composition, comprising adding at least one hyperbranched polyol and at least one acrylic film former to the composition are provided Unless otherwise indicated, all numbers expressing quantities of ingredients, reaction conditions, and so forth used in the specification and claims are to be understood as being modified in all instances by the term "about." Accordingly, unless indicated to the contrary, the numerical parameters set forth in the following specification and attached claims are approximations that may vary depending upon the desired properties sought to be obtained by the present invention.

Notwithstanding that the numerical ranges and parameters setting forth the broad scope of the invention are approximations, the numerical values set forth in the specific examples are reported as precisely as possible. Any numerical value, however, inherently contain certain errors necessarily resulting from the standard deviation found in their respective measurements. The following examples are intended to illustrate the invention without limiting the scope as a result. The percentages are given on a weight basis.

EXAMPLES

The following compositions were prepared:

Example 1

Lipstick

| Ingredient | Weight % |
|---|---|
| C20-24 olefin/oleyl alcohol | 18.79% |
| Synamer | 38% |
| isohexadecane | 21.57% |
| hydrogenated polyisobutene | 3.1% |
| octyldodecyl neopentanoate | 4.8% |
| bis-behenyl/isostearyl/phytosteryl dimer dilinoleate | 5.15% |
| Vp/hexadecene copolymer | 6.6% |
| polyethylene | 5.5% |
| polyethylene | 5.5% |
| VP/eicosane copolymer | 1% |
| polyglycerol 3 beeswax | 1.7% |
| Red 7 | 4% |
| mica | 5.3% |
| HDI/trimethylol hexylactone | 1% |

Procedure:

The oils, waxes and synamer-3 were combined and heated at 100° C., and mixed at 250 rpm until clear. The pigments were then added and mixed. Fillers were then added. Then, the hyperbranched polyol was added. The composition was cooled to 92° C. and poured.

The invention lipstick resulted in a very shiny product after application, which provided shine, cushion and creaminess upon application.

Example 2

Lipstick

| Ingredient | Weight % |
|---|---|
| C20-24 olefin/oleyl alcohol | 15% |
| Acrylic acid/isobutyl acrylate/ Isobornyl acrylate copolymer | 15% |
| hydrogenated polyisobutene | 10.65% |
| octyldodecyl neopentanoate | 15% |
| trimethylsiloxyphenyl dimethicone | 20% |
| squalane | 12% |
| octyldodecanol | 0.7% |
| titanium dioxide | 0.06% |
| red 28 | 0.07% |
| yellow 6 | 0.27% |
| black iron oxide | 0.12% |
| Red 7 | 0.23% |
| Mica | 4.75% |

Example 3

Lipstick

| Ingredient | Weight % |
| --- | --- |
| C20-24 olefin/oleyl alcohol | 18.79% |
| Synamer (50% solids) | 38% |
| Regalite | 8% |
| isohexadecane | 21.57% |
| hydrogenated polyisobutene | 3.1% |
| octyldodecyl neopentanoate | 4.8% |
| bis-behenyl/isostearyl/phytosteryl dimer dilinoleate | 5.15% |
| Vp/hexadecene copolymer | 6.6% |
| polyethylene | 5.5% |
| polyethylene | 5.5% |
| VP/eicosane copolymer | 1% |
| polyglycerol 3 beeswax | 1.7% |
| Red 7 | 4% |
| mica | 5.3% |
| HDI/trimethylol hexylactone | 1% |

Example 4

Lipstick

| Ingredient | Weight |
| --- | --- |
| C20-24 olefin/oleyl alcohol | 18.79% |
| Synamer (50% solids) | 4% |
| Regalite | 8% |
| isohexadecane | 21.57% |
| hydrogenated polyisobutene | 3.1% |
| octyldodecyl neopentanoate | 8.8% |
| bis-behenyl/isostearyl/phytosteryl dimer dilinoleate | 5.15% |
| Vp/hexadecene copolymer | 6.6% |
| polyethylene | 5.5% |
| polyethylene | 5.5% |
| VP/eicosane copolymer | 1% |
| polyglycerol 3 beeswax | 1.7% |
| Red 7 | 4% |
| mica | 5.3% |
| HDI/trimethylol hexylactone | 1% |

This lipstick resulted in a very shiny product after application, which was adherent and smooth after application.

What is claimed is:

1. A composition comprising at least one hyperbranched alcohol functional olefinic polymer which is a C20-C24 olefin/oleyl alcohol, at least one acrylic film former comprising at least one (meth)acrylic ester comprising at least one alkyl group comprising 4 to 14 carbon atoms and at least one acrylic acid, and at least one oil, wherein at least one hyperbranched alcohol functional olefinic polymer has a hydroxyl number of 15 to 150 and the hyperbranched alcohol functional polymer(s) represent from 1% to 30% of the total weight of the composition, the acrylic film former(s) represent from 0.1% to 30% of the total weight of the composition, and wherein the hyperbranched alcohol functional olefinic polymer(s) and the film former(s) are present in a weight ratio of between 10:1 and 1:1.

2. The composition of claim 1, wherein the composition further comprises at least one coloring agent.

3. The composition of claim 1, wherein the composition further comprises at least one tackifier and the at least one tackifier represents from 1% to 20% of the total weight of the composition.

4. The composition of claim 1, wherein the composition is anhydrous.

5. The composition of claim 1, wherein the film former(s) represent from 1% to 20% of the total weight of the composition.

6. The composition of claim 1, wherein the hyperbranched alcohol functional olefinic polymer and the film former are present in a weight ratio of between 7:1 and 1.5:1.

7. The composition of claim 3, wherein the hyperbranched alcohol functional olefinic polymer and the film former are present in a weight ratio of between 7:1 and 1.5:1.

8. The composition of claim 1, wherein the oil(s) are present in an amount ranging from 5% to 60% by weight based on the total weight of the composition.

9. The composition of claim 1, further comprising at least one wax.

10. The composition of claim 1, wherein the at least one oil is a volatile oil.

11. The composition of claim 10, wherein the volatile oil(s) are present in an amount ranging from 10% to 40% by weight with respect to the total weight of the composition.

12. The composition of claim 3, wherein the at least one tackifier is a hydrogenated styrene/methyl styrene/indene copolymer.

13. A method of making up lips comprising applying the composition of claim 1 to the lips.

14. The composition of claim 5, wherein the hyperbranched alcohol functional olefinic polymer and the film former are present in a weight ratio of between 7:1 and 1.5:1.

15. The composition of claim 12, wherein the hyperbranched alcohol functional olefinic polymer and the film former are present in a weight ratio of between 7:1 and 1.5:1.

16. A method of making up lips comprising applying the composition of claim 5 to the lips.

17. A method of making up lips comprising applying the composition of claim 12 to the lips.

18. The composition of claim 1, wherein the at least one acrylic film former comprises at least one (meth)acrylic ester comprising at least one alkyl group comprising 4 to 9 carbon atoms.

19. The composition of claim 1, wherein the at least one acrylic film former comprises at least one (meth)acrylic ester selected from the group consisting of n-butyl acrylate, n-butyl methacrylate, n-pentyl acrylate, n-pentyl methacrylate, n-amyl acrylate, n-hexyl acrylate, hexyl methacrylate, n-heptyl acrylate, n-octyl acrylate, n-octyl methacrylate, n-nonyl acrylate, isobutyl acrylate, isooctyl acrylate, isooctyl methacrylate, 2-ethylhexyl acrylate and 2-ethylhexyl methacrylate.

20. The composition of claim 1, wherein the acrylic film former copolymer further comprises at least one vinylically functionalized monomer.

* * * * *